United States Patent [19]

Gustavson et al.

[11] Patent Number: 5,420,105
[45] Date of Patent: May 30, 1995

[54] POLYMERIC CARRIERS FOR NON-COVALENT DRUG CONJUGATION

[76] Inventors: Linda M. Gustavson, 19809 - 31st St., NE., Seattle, Wash. 98155; David C. Anderson, 200 Lassen Dr., San Bruno, Calif. 94066; Alton C. Morgan, Jr., 803 Driftwood Pl., Edmonds, Wash. 98020

[21] Appl. No.: 95,515

[22] Filed: Jul. 26, 1993

Related U.S. Application Data

[63] Continuation-in-part of Ser. No. 248,456, Sep. 23, 1988, Pat. No. 5,252,713.

[51] Int. Cl.$^6$ ............ A61K 31/415; A61K 47/42; A61K 47/48
[52] U.S. Cl. ............................. 514/2; 424/178.1; 514/8; 514/387; 530/350; 530/363; 530/367; 530/370; 530/392; 530/409; 548/304.1
[58] Field of Search ............ 514/2, 8, 387; 435/188; 530/350, 351, 362, 363, 387.3, 392, 399, 391.7, 391.9, 402, 367, 370, 409, 825; 424/85.91, 178.1; 548/303.7, 304.1

[56] References Cited

U.S. PATENT DOCUMENTS

| | | | |
|---|---|---|---|
| 4,863,713 | 9/1989 | Goodwin et al. | 424/1.1 |
| 4,948,590 | 8/1990 | Hawrot et al. | 436/829 |
| 5,106,951 | 4/1992 | Morgan, Jr. et al. | 530/405 |
| 5,204,448 | 4/1993 | Subramanian | 530/409 |
| 5,225,325 | 7/1993 | Miller et al. | 435/188 |
| 5,252,713 | 10/1993 | Morgan, Jr. et al. | 530/371.7 |
| 5,273,743 | 12/1993 | Ahlem et al. | 530/387.3 |
| 5,283,342 | 2/1994 | Gustavson et al. | 436/808 |
| 5,328,985 | 7/1994 | Sano et al. | 435/7.1 |

OTHER PUBLICATIONS

J. Immunology, vol. 139, No. 7, issued 01 Oct. 1987, Glennie et al, "Preparation and Performance of Bispecific . . . ", pp. 2367–2375.

Primary Examiner—Jeffrey E. Russel

[57] ABSTRACT

Polymeric carriers are polypeptides comprising at least one drug-binding domain that non-covalently binds a drug. A polymeric carrier may be attached to an antibody specific for desired target cells to form immunoconjugates that deliver a drug to the target cells in vivo. A polymeric carrier may be attached to a proteinaceous or a non-proteinaceous ligand or anti-ligand to form a conjugate useful in pretargeting protocols to deliver a drug to target cells in vivo. The carriers are derived from drug-binding proteins and produced through peptide synthesis or recombinant DNA technology.

14 Claims, 1 Drawing Sheet

POLYMERIC CARRIERS FOR NON-COVALENT DRUG CONJUGATION

CROSS REFERENCE TO RELATED APPLICATIONS

This application is a continuation-in-part of U.S. patent application Ser. No. 07/248,456, filed Sep. 23, 1988, now U.S. Pat. No. 5,252,713.

TECHNICAL FIELD

The present invention relates to compositions and methods for making polymeric carriers for non-covalent binding of drugs. The polymeric carriers are capable of binding one or multiple drug molecules. The polymeric carriers are then covalently attached to a targeting protein, such as an antibody molecule, thereby forming an antibody/polymeric carrier/drug conjugate for targeting to defined populations of cells, such as cancer cells.

BACKGROUND OF THE INVENTION

There has been considerable interest in developing methods of attaching various diagnostic and therapeutic agents to targeting proteins such as antibodies. Recent efforts include the conjugation of therapeutic agents, such as cytotoxic or antineoplastic drugs, to specific antibodies, such as monoclonal antibodies, to produce conjugates which can selectively target tumor cells while sparing normal tissues.

A large number of different classes of therapeutic agents have been considered, including beta-, gamma-, and alpha-emitting radioisotopes; plant and bacterial toxins; and a variety of antineoplastic drugs, including intercalating agents, antimetabolites, alkylating agents, and antibiotics. It is desirable to conjugate chemotherapeutic drugs to targeting molecules such as antibodies for the following reasons:

1. It has recently been shown that up to 1,000-fold more drug can be delivered to tumor cells when conjugated to an antigen-specific monoclonal antibody than is possible by the addition of free drug.

2. Pleiotropic drug resistance may arise following treatment with one of a number of chemotherapeutic drugs, resulting in inducing resistance to drugs of several classes. The mechanism(s) of this resistance are not entirely known, but it is known that this resistance can be partially overcome by antibody targeting of drugs.

3. Even though current chemotherapeutic drugs are active against only some of the major tumor types, the response rate in drug-insensitive tumor types may be increased by antibody-mediated delivery.

4. Many dose-limiting toxicities which are now seen with chemotherapeutic drugs can be reduced by conjugation to an antibody. A decrease in toxicity with concomitantly at least equal efficacy would provide a superior product with a higher therapeutic index.

To create a conjugate with a therapeutic agent and an antibody, the therapeutic agent may be directly linked to the antibody through nucleophilic substitution of certain groups on the antibody (e.g., amino, carboxyl, or sulfhydryl) or the drug may be conjugated to the antibody via a hetero- or homobifunctional cross-linker.

The linking group generally is heterobifunctional, having two different functionalities, one of which reacts with the drug and the other with the antibody. Linking groups may be small or quite long. For example, a relatively small linking group is carbonyl diimidazole.

Large proteins or polymers ("carriers") have also been used as linking groups and offer the advantage of being able to bind many drug molecules to a single antibody molecule. Examples of large proteins or polymers are poly-L-lysine, polyglutamate, dextran, and albumin, all of which have molecular weights in excess of 5000 daltons. These carriers generally are derivatized with small linking groups to bind drugs. See, for example, U.S. Pat. Nos. 4,699,784 and 4,046,722.

Drug conjugation to a protein or an antibody targeting molecule has generally been through covalent binding of the drug to the antibody directly or by covalently binding the drug molecule to the linking group. (Blair et al., *J. Immunol. Meth.* 59:129–44, 1983.) Even when the drug is linked to a carrier molecule such as albumin or dextran, the drug undergoes a modification to allow for the covalent conjugation of the drug. The drug modification often results in the loss of some of the activity of the drug molecule due to chemical modifications of some of the functional groups within the drug molecule.

In the case of some drug molecules, exposure to derivatization conditions may completely inactivate the drug. For other drug molecules, the derivatization may not be completely specific for groups intended for linkage but may also modify groups important for drug activity.

In contrast to such "drug-antibody" administration procedures, pretargeting approaches may be used to achieve therapeutic or diagnostic goals. Pretargeting approaches involve the interaction of two members of a high affinity binding pair such as a ligand-anti-ligand binding pair. Pretargeting is characterized by an uncoupling of the kinetics of the targeting moiety capable of localizing to a target site in vivo and the diagnostic or therapeutic active agent. This decoupling of the relatively slow localization kinetics of targeting moiety localization from the faster clearing active agent affords lower non-target exposure.

Accordingly, there exists a need in the field of drug conjugation to be able to attach multiple drug molecules to the targeting antibody, ligand or anti-ligand without covalent modification of the drug and loss of drug activity.

SUMMARY OF THE INVENTION

The present invention provides polymeric carriers comprising at least one drug-binding domain derived from a protein, wherein each drug-binding domain can non-covalently bind a drug. The polymeric carrier preferably comprises multiple drug-binding domains, wherein the domains may be the same or different and therefore may bind the same or different drugs.

The polymeric carrier may be attached to a targeting protein, such as an antibody, that binds to a desired target site in vivo. The present invention thus provides targeting protein/polymeric carrier/drug conjugates comprising a targeting protein covalently bound to a polymeric carrier, wherein said polymeric carrier comprises one or more drug-binding domains having a drug non-covalently bound thereto, wherein each of said domains is derived from a drug-binding protein. The targeting protein may be covalently bonded to the polymeric carrier directly or through a linker molecule. Pharmaceutical preparations comprising such a conjugate in an aqueous solution (for in vivo administration for therapeutic purposes) also are disclosed.

The polymeric carrier may also be attached to a member of a high affinity binding pair, e.g., a ligand-anti-ligand binding pair as discussed herein. Such polymeric carrier-containing compounds may include one or more ligand or anti-ligand molecules. When one member of a ligand-anti-ligand pair (e.g., an anti-ligand) is localized to a target site via a targeting moiety such as a monoclonal antibody or the like, the binding pair member (anti-ligand) serves to target a subsequently administered complementary binding pair member (ligand)-active agent conjugate to target sites characterized by previously localized targeting moiety-binding pair member (anti-ligand). Such pretargeting methods useful in both diagnostic and therapeutic applications are also discussed.

The present invention thus provides a binding pair member/polymeric carrier/drug conjugate comprising a ligand or anti-ligand covalently bound to a polymeric carrier, wherein said polymeric carrier comprises one or more drug-binding domains having a drug non-covalently bound thereto, wherein each of said domains is derived from a drug-binding protein. One or more ligand or anti-ligand molecules may be covalently bonded to the polymeric carrier directly or through a linker molecule. An example of a ligand is biotin, with the complementary anti-ligand thereof being avidin or streptavidin, wherein biotin and avidin or streptavidin together form a ligand-anti-ligand binding pair. Pharmaceutical preparations comprising such a conjugate in an aqueous solution (for in vivo administration for therapeutic purposes) also are disclosed.

The present invention also provides methods for producing polymeric carriers. The carriers are derived from relatively large molecular weight proteins, and may be produced by such methods as peptide synthesis or recombinant DNA technology.

A method for preserving the therapeutic activity of a drug also is disclosed, said method comprising non-covalently binding the drug to a polymeric carrier. The drug activity is thus preserved during subsequent chemical reactions, such as the reactions used to attach the polymeric carrier to a targeting protein to form a conjugate. Drug activity also is preserved in vivo after administration of the conjugate to a human or mammalian host.

DETAILED DESCRIPTION OF THE INVENTION

Prior to describing the invention in detail, it is helpful to set forth certain definitions.

Polymeric Carrier: By the term "polymeric carrier" is meant a polymer, such as a polypeptide, comprising one or more drug-binding domains wherein the domains are capable of binding a drug through non-covalent bonds. The polymeric carriers of the present invention are not naturally occurring, but are derived from naturally occurring proteins. A polymeric carrier may comprise one or multiple drug-binding domains fabricated through such methods as peptide synthesis or recombinant DNA technology. The domains may then be polymerized to produce a multi-domain polymeric carrier. A polymeric carrier of the present invention is able to non-covalently bind at least one drug through one or more non-covalent interactions or reversible interactions.

Covalent Bond: A "covalent bond" is defined as the formation of a sigma bond between two organic molecules.

Non-covalent Bond: A "non-covalent bond" is meant to include all interactions other than a covalent bond. Non-covalent bonds include ionic interactions, hydrogen bonding, pi-pi bonding, hydrophobic interactions, and van der Waals interactions.

Targeting moiety: A molecule that binds to a defined population of cells. The targeting moiety may bind a receptor, an oligonucleotide, an enzymatic substrate, an antigenic determinant, or other binding site present on or in the target cell population. Targeting moieties that are proteins are referred to herein as "targeting proteins." Antibody is used throughout the specification as a prototypical example of a targeting moiety and a targeting protein. Tumor is used as a prototypical example of a target in describing the present invention.

Ligand/anti-ligand Pair: A complementary/anti-complementary set of molecules that demonstrate specific binding, generally of relatively high affinity. Exemplary ligand/anti-ligand pairs include zinc finger protein/dsDNA fragment, hapten/antibody, lectin/carbohydrate, ligand/receptor, and biotin/avidin. Biotin/avidin is used throughout the specification as a prototypical example of a ligand/anti-ligand pair.

Anti-ligand: As defined herein, an "anti-ligand" demonstrates high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Anti-ligands of the present invention may exhibit or be derivatized to exhibit structural features that direct the uptake thereof, e.g., galactose residues that direct liver uptake. Avidin and streptavidin are used herein as prototypical anti-ligands.

Avidin and Streptavidin: As defined herein, both of the terms "avidin" and "streptavidin" include avidin, streptavidin and derivatives and analogs thereof that are capable of high affinity, multivalent or univalent binding of biotin.

Ligand: As defined herein, a "ligand" is a relatively small, soluble molecule that exhibits rapid serum, blood and/or whole body clearance when administered intravenously in an animal or human. Biotin is used as the prototypical ligand.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step and other related methods described herein are also encompassed.

The present invention addresses the problem of loss of drug activity due to attachment of drugs to various carriers through covalent bonds. Briefly stated, the present invention relates to a polymeric carrier containing one or multiple drug-binding domains (wherein each drug-binding domain non-covalently binds a drug), conjugates comprising a polymeric carrier bound to a targeting protein, ligand or anti-ligand, and conjugates comprising one or more drug molecules non-covalently bound to a polymeric carrier which in turn is bound to a targeting protein, ligand or anti-ligand.

The targeting protein is a protein that binds to a desired target site in vivo, thereby delivering the conjugate to the target site. Targeting proteins include antibodies as well as proteinaceous ligands or anti-ligands, and are described in more detail below.

Ligands suitable for use within the present invention include biotin, haptens, lectins, epitopes, dsDNA fragments and analogs and derivatives thereof. Useful complementary anti-ligands include avidin (for biotin), carbohydrates (for lectins), antibody, fragments or analogs thereof, including mimetics (for haptens and epitopes) and zinc finger proteins (for dsDNA fragments). Preferred ligands and anti-ligands bind to each other with an affinity of at least about $k_D \geq 10^{-9} M$.

Also provided by the present invention are conjugates comprising a polymeric carrier as a drug active site protecting group. The polymeric carrier serves to protect the drug's active functional groups during the chemical reactions used to attach the polymeric carrier to a targeting protein. The polymeric carrier also protects the drug after in vivo administration of a drug(s)-/polymeric carrier/targeting protein conjugate and minimizes nonspecific interactions of the drug moiety of the conjugate with cellular membranes.

Polymeric carriers are polymers such as polypeptides comprising one or a plurality of drug binding domains, which may be produced by such methods as peptide synthesis procedures or through cloning and expression of specific nucleotide sequences. The polymeric carrier preferably contains multiple drug-binding domains, wherein the drug-binding domain may be derived from a large molecular weight polymer such as a protein and then polymerized. The large protein can typically bind non-covalently only one or a few drug molecules. The polymeric carrier polypeptides may be synthesized as a single polypeptide chain or as disulfide-bonded peptide chains.

In another aspect, the present invention provides a method for producing polymeric carriers. These carriers are prepared by first identifying a protein, generally a large molecular weight protein, that is able to non-covalently bind a particular drug of interest. A drug-binding domain is then isolated from the protein, wherein the drug-binding domain is capable of binding a drug of interest through non-covalent means. Examples of large molecular weight proteins that can non-covalently bind to certain drug molecules include, but are not limited to, riboflavin-binding protein (RBP) to anthracyclines; albumin to certain lipophilic drugs such as anthracyclines, methotrexate, and cis-platinum; or one of the other proteins described below (e.g., in Table I).

Once the drug-binding domain in such proteins is identified and characterized (e.g., by determination of the amino acid sequence), the polymeric carriers may be produced through a variety of techniques. Such techniques include peptide synthesis to produce multiple copies of the domain, which may be joined to form a multi-domain polymeric carrier. Alternatively, single or multiple domain polymeric carriers may be produced through recombinant DNA technology.

Another aspect of the invention is a pharmaceutical composition which includes a conjugate comprising one or more drug molecules bound to a single- or multiple-domain polymeric carrier for prolonged serum half-life and increased efficacy. These slow-release pharmaceutical compositions may include a conjugate comprising a drug non-covalently bound to a polymeric carrier which in turn may be attached to a targeting protein, ligand or anti-ligand. Preferably, such conjugates are formed by covalently conjugating the polymeric carrier to ligand or anti-ligand, for example, wherein this conjugation is followed by non-covalent attachment of drug to the polymeric carrier-ligand or -anti-ligand compound. Alternatively, the conjugate may comprise a polymeric carrier bound to a targeting protein, ligand or anti-ligand wherein the drug is to be added and non-covalently bound later, before use. The non-covalent binding of the drug in the conjugates of the present invention permits slow release of the drug from the polymeric carrier in vivo. "Slow release" means that the serum half life of the drug is increased compared to free drug. The patient's tissues are exposed to the drug for a longer period of time than when free (i.e., unconjugated) drug is administered, and therapeutic efficacy thus is enhanced.

It is preferable to isolate a drug-binding domain from a large molecular weight protein to form the conjugates of the invention because attaching a high molecular weight protein to a targeting protein may have an adverse effect on the desired biological activity (e.g., the "targeting" ability) of the targeting protein. For example, attaching the large protein to an antibody may impair the immunoreactivity and accessibility to tumors of the resulting immunoconjugate. This is especially true if more than one high molecular weight protein molecule is attached to a targeting protein molecule. For example, RBP is a 50-kilodalton glycoprotein that binds one mole of drug per mole of protein. Conjugation of multiple RBPs per antibody molecule would result in a conjugate with a molecular weight unacceptable for rapid extravasation and delivery to tumor sites. Accordingly, the use of just the drug-binding domain of RBP polymerized to give a polymeric carrier with multiple drug-binding domains would provide for non-covalent binding and delivery to target sites of multiple drug molecules per targeting protein, ligand or anti-ligand, while reducing the size of the carrier protein to which the drug molecules are bound. The total molecular weight of the multi-domain polymeric carrier preferably is less than about 60,000 daltons.

Non-covalent binding of the drug preserves the activity of the drug, as discussed above. A polymeric carrier also serves to protect the active functional groups on the drug molecule by non-covalently binding to the drug molecule. The enveloping of the drug by the polymeric carrier serves to protect the functional groups of the drug molecule from any subsequent derivatization conditions (used to conjugate the carrier to the targeting protein, ligand or anti-ligand) and to block nonspecific interactions between the drug functional groups and non-target cell surfaces during in vivo administration of the targeting protein, ligand or anti-ligand conjugate.

The process of isolating a polymeric carrier from a drug-binding, large molecular weight protein begins with the identification of a large protein that can non-covalently bind the drug of interest. Examples of such protein/drug pairs are shown in Table I. The drugs in the Table (other than the steroids) are anti-cancer drugs.

TABLE I

| PROTEIN | DRUG |
| --- | --- |
| Riboflavin-Binding Protein | Doxorubicin, daunorubicin, and other anthracyclines |
| Alpha-1-acid glycoprotein | Doxorubicin, daunorubicin, other anthracyclines, vinblastine, mitoxantrone, ARA-C, 6-mercaptopurine, 6-mercaptoguanosine, and mitomycin C |
| Steroid-binding protein | Testosterone, estrogen derivatives |
| Estrogen receptor | Estrogens and derivatives thereof |
| Albumin | Doxorubicin, daunorubicin, other anthracyclines, cis-platinum, methotrexate |

Other drug-binding proteins may be identified by appropriate analytical procedures, including Western blotting of large proteins or protein fragments and subsequent incubation with a detectable form of drug. Alternative procedures include combining a drug and a protein in a solution, followed by size exclusion HPLC gel filtration, thin-layer chromatography (TLC), or other analytical procedures that can discriminate between free and protein bound drug. Detection of drug binding can be accomplished by using radiolabeled, fluorescent, or colored drugs and appropriate detection methods. Equilibrium dialysis with labeled drug may be used. Alternative methods include monitoring the fluorescence change that occurs upon binding of certain drugs (e.g., anthracyclines or analogs thereof, which should be fluorescent). In one detection method, drug and protein are mixed, and an aliquot of this solution (not exceeding 5% of the column volume of an HPLC column, such as a Biosil TSK-250 $7.5 \times 30$ cm column) is loaded onto the HPLC column. The flow rate is 1 ml/min. The drug bound to protein will elute first, in a separate peak, followed by free drug, eluting at a position characteristic of its molecular weight. If the drug is doxorubicin, both a 280-nm as well as a 495-nm adsorptive peak will correspond to the elution position of the protein if interaction occurs. The elution peaks for other drugs will indicate whether drug binding occurs.

Knowledge of the chemical structure of a particular drug (i.e., whether chemically reactive functional groups are present) allows one to predict whether covalent binding of the drug to a given protein can occur. Additional methods for determining whether drug binding is covalent or non-covalent include incubating the drug with the protein, followed by dialysis or subjecting the protein to denaturing conditions. Release of the drug from the drug-binding protein during these procedures indicates that the drug was non-covalently bound. Usually, a dissociation constant of about $10^{-15}$M or less indicates covalent or extremely tight non-covalent binding.

During dialysis, non-covalently bound drug molecules are released over time from the protein and pass through a dialysis membrane, whereas covalently bound drug molecules are retained on the protein. An equilibrium constant of about $10^{-5}$M indicates non-covalent binding. Alternatively, the protein may be subjected to denaturing conditions; e.g., by gel electrophoresis on a denaturing (SDS) gel or on a gel filtration column in the presence of a strong denaturant such as 6M guanidine. Covalently bound drug molecules remain bound to the denatured protein, whereas non-covalently bound drug molecules are released and migrate separately from the protein on the gel and are not retained with the protein on the column.

Once a protein that can non-covalently bind a particular drug of interest is identified, the drug-binding domain is identified and isolated from the protein by any suitable means. Protein domains are portions of proteins having a particular function or activity (in this case, non-covalent binding of drug molecules). The present invention provides a process for producing a polymeric carrier, comprising the steps of generating peptide fragments of a protein that is capable of non-covalently binding a drug and identifying a drug-binding peptide fragment, which is a peptide fragment containing a drug-binding domain capable of non-covalently binding the drug, for use as the polymeric carrier.

One method for identifying the drug-binding domain begins with digesting or partially digesting the protein with a proteolytic enzyme or specific chemicals to produce peptide fragments. Examples of useful proteolytic enzymes include lys-C-endoprotease, arg-C-endoprotease, V8 protease, endoprolidase, trypsin, and chymotrypsin. Examples of chemicals used for protein digestion include cyanogen bromide (cleaves at methionine residues), hydroxylamine (cleaves the Asn-Gly bond), dilute acetic acid (cleaves the Asp-Pro bond), and iodosobenzoic acid (cleaves at the tryptophane residue). In some cases, better results may be achieved by denaturing the protein (to unfold it), either before or after fragmentation.

The fragments may be separated by such procedures as high pressure liquid chromatography (HPLC) or gel electrophoresis. The smallest peptide fragment capable of drug binding is identified using a suitable drug-binding analysis procedure, such as one of those described above. One such procedure involves SDS-PAGE gel electrophoresis to separate protein fragments, followed by Western blotting on nitrocellulose, and incubation with a colored drug like adriamycin. The fragments that have bound the drug will appear red. Scans at 495 nm with a laser densitometer may then be used to analyze (quantify) the level of drug binding.

Preferably, the smallest peptide fragment capable of non-covalent drug binding is used. It may occasionally be advisable, however, to use a larger fragment, such as when the smallest fragment has only a low-affinity drug binding domain.

The amino acid sequence of the peptide fragment containing the drug-binding domain is elucidated. The purified fragment containing the drug-binding region is denatured in 6M guanidine hydrochloride, reduced and carboxymethylated by the method of Crestfield et al., *J. Biol. Chem.* 238:622, 1963. As little as 20 to 50 picomoles of each peptide fragment can be analyzed by automated Edman degradation using a gas-phase or liquid-pulsed protein sequencer (commercially available from Applied Biosystems, Inc.). If the peptide fragment is longer than 30 amino acids, it will most likely have to be fragmented as above and the amino acid sequence patched together from sequences of overlapping fragments.

Once the amino acid sequence of the desired peptide fragment has been determined, the polymeric carriers can be made by either one of two types of synthesis. The first type of synthesis comprises the preparation of each peptide chain with a peptide synthesizer (e.g., commercially available from Applied Biosystems). The second method utilizes recombinant DNA procedures.

Peptide amides can be made using 4-methylbenzhydrylamine-derivatized, cross-linked polystyrene- 1% divinylbenzene resin and peptide acids made using PAM (phenylacetamidomethyl) resin (Stewart et al., "Solid Phase Peptide Synthesis," Pierce Chemical Company, Rockford, Ill., 1984). The synthesis can be accomplished either using a commercially available synthesizer, such as the Applied Biosystems 430A, or manually using the procedure of Merrifield et al., Biochemistry 21:5020–31, 1982; or Houghten, PNAS 82:5131–35, 1985. The side chain protecting groups are removed using the Tam-Merrifield low-high HF procedure (Tam et al., J. Am. Chem. Soc. 105:6442–55, 1983). The peptide can be extracted with 20% acetic acid, lyophilized, and purified by reversed-phase HPLC on a Vydac C-4 Analytical Column using a linear gradient of 100% water to 100% acetonitrile-0.1% trifluoroacetic acid in 50 minutes. The peptide is analyzed using PTC-amino acid analysis (Heinrikson et al., Anal. Biochem. 136:6c-74, 1984). After gas-phase hydrolysis (Meltzer et al., Anal. Biochem. 160:356–61, 1987), sequences are confirmed using the Edman degradation or fast atom bombardment mass spectroscopy. After synthesis, the polymeric carriers can be tested for drug binding using size-exclusion HPLC, as described above, or any of the other analytical methods listed above.

The polymeric carriers of the present invention preferably comprise more than one drug-binding domain. A polypeptide comprising several drug-binding domains may be synthesized. Alternatively, several of the synthesized drug-binding peptides may be joined together using bifunctional cross-linkers, as described below.

The second synthetic mechanism involves the determination of a DNA sequence which will encode the desired amino acid sequence (i.e., the amino acid sequence of the drug-binding peptide fragment: determined above). Such a DNA sequence may be determined because the genetic code (i.e., the three-base sequence or codon in an mRNA which specifies a given amino acid) is known. A DNA sequence which encodes the polymeric carrier may be synthesized in in vitro by standard oligonucleotide synthesis procedures. See, for example, U.S. Pat. Nos. 4,500,707 and 4,668,777. The synthetic DNA fragment encoding the polymeric carrier is cloned and expressed using recombinant DNA technology.

When a polymeric carrier containing multiple copies of a drug-binding domain is desired, a DNA sequence that encodes a polypeptide comprising multiple copies of the drug-binding peptide fragment is synthesized. Alternatively, multiple copies of the oligonucleotide encoding the domain may be ligated together by conventional procedures (e.g., using the enzyme T4 DNA ligase). The resulting DNA sequence encodes a polypeptide comprising multiple drug-binding domains. Such polypeptides are useful as polymeric carriers that bind several drug molecules non-covalently. The DNA sequences encoding these polymeric carriers may be cloned and expressed through recombinant DNA technology.

Many suitable methods for inserting a DNA sequence of interest into a microbial host to generate recombinant microorganisms which produce the polypeptide encoded by the DNA are known. Microorganisms which have been used as host cells include, but are not limited to, prokaryotes, such as gram-negative and gram-positive bacteria, and eukaryotes, such as yeast or mammalian cell lines. In general, the DNA sequence is inserted in vitro into a vector capable of replication in certain host microorganisms. The vector typically is derived from a plasmid or a virus.

A number of cloning vector/host cell systems have been developed including vectors suitable for transforming the gram-negative bacterium E. coli (Old and Primrose, Principals Of Gene Manipulation, 2d ed., Univ. of California Press, 1981, pp. 32–35 and 46–47), gram-positive bacteria Bacillus subtilis (Old and Primrose, pp. 51–53), or eukaryotic microorganisms such as yeast (Old and Primrose, pp. 62–68) "Shuttle vectors," which may be transferred (along with the cDNA they carry) between the host microorganisms, E. coli and yeast, have been described by Storms et al., J. Bacteriology 140:73–82, 1979; and Blanc et al., Molec. Gen. Genet. 176:335–42, 1979. Shuttle vectors also exist which replicate in both E. coli and B. subtilis (Old and Primrose, at p. 53). Vectors derived from bacteriophages such as M13 have also been useful in the cloning of foreign genes (Old and Primrose, Chapter 5).

Known procedures are used for inserting the DNA into a suitable vector, e.g., homopolymeric tailing, blunt-end ligation, or by use of linker molecules (Old end Primrose, at p.92). Microbial host cells are transformed with the resulting recombinant cloning vectors, and the transformants are screened using conventional procedures, which vary according to the particular gene and vector/host system used to identify transformants containing the desired cloned cDNA.

The cloned DNA sequence generally is transferred to an appropriate "expression vector," although certain vectors that have been developed play the dual roles of both cloning and expression vectors. An expression vector comprises "expression signals," i.e., sequences such as promotors and operators, which are required for the transcription of DNA into messenger RNA (mRNA). This is followed by translation of the mRNA into protein (i.e., the polypeptide encoded by the DNA sequence). The expression signals are functional in the intended host cell. The DNA sequence of interest is "operably linked" to the expression signals by insertion of the DNA into the vector in a position downstream from the expression signals such that the first codon of the protein-encoding sequence is in the same reading frame as an initiation codon. Examples of some of the many expression vectors which have been developed for use in recombinant DNA technology include those described by Old and Primrose, pp. 104–17; PCT Patent Application Publication No. WO 86/00528; U.S. Pat. Nos. 4,599,311 and 4,704,362; and British Patent No. GB 2,119,804.

An appropriate microorganism strain is transformed with the recombinant expression vector, then cultured in a suitable growth medium under conditions appropriate for production of the desired polypeptide. Expression vector systems may be engineered so that expression of the foreign protein may be regulated by chemical or temperature induction. Proteins which are secreted out of the host cells may be isolated from the growth media by conventional protein purification procedures. When the desired protein remains inside the host cells, the cells are harvested and then lysed through procedures which may be mechanical (e.g., sonication, homogenization, freeze-thawing, nitrogen compression-decompression, etc.), chemical (e.g., treatment with detergents such as sodium dodecyl sulfate, guanidine HCl or NP-40), enzymatic (such as by using lysozyme), or combinations thereof. The desired polypeptide is then purified from the lysate using conventional procedures.

The polypeptides produced by cloning and expressing DNA sequences encoding one or more drug-binding domains are used as polymeric carriers. The recombinant cells may be cultured to produce large quantities of the polymeric carrier polypeptides, and these carriers may be attached to various targeting proteins to form conjugates capable of non-covalently binding drug molecules.

When the amino acid sequence of a drug-binding protein is known, drug-binding domains can be isolated without prior enzymatic or chemical digestion of the protein. For example, the sequence of chicken riboflavin-binding protein is known (Protein Information Resource Protein Sequence Data Bank). In order to search for a riboflavin-binding domain, 40-amino-acid-long peptides, overlapping by 20 amino acids, can be synthesized from the known sequence of this 219-residue protein. The peptides are synthesized as described above, using manual procedures or a commercially available synthesizer. Each synthetic peptide can then be tested for drug binding. By comparison of the sequence of the overlapping peptides which bind drugs, those residues important for drug binding can be identified. A peptide comprising the drug-binding domain can then be replicated and conjugated to form a polymeric carrier according to the procedures described below.

When several proteins are known to bind the same or similar drugs, it may be possible to identify the drug binding domain within each of the proteins by identifying homologous amino acid sequences within the proteins. Alternatively, when the amino acid sequence of the drug-binding domain of one protein that binds a drug of interest is known, a computer search for homologous sequences may be run on a large protein sequence data bank. Additional proteins that may bind the particular drug of interest thus may be found. Through either of these approaches, drug-binding domains may be identified without running drug-binding assays on a large number of peptide fragments representing the entire amino acid sequence of a protein.

Another process for isolating a polymeric carrier involves cloning the gene which encodes a large molecular weight protein that can non-covalently bind to a drug of interest. Procedures for isolating and cloning DNA sequences which encode such proteins are known. See, for example, Lawn et al., *Nucleic Acids Research* 9:6103–14, 1981, in which isolation of cDNA which encodes the human serum albumin (HSA) protein is described.

A cloned gene encoding a drug-binding protein may be isolated from a recombinant microorganism and fragmented using restriction endonucleases. The resulting gene fragments are subcloned and expressed in a suitable host/vector system, thereby producing fragments of the drug-binding protein. The peptide fragments produced by the various recombinant microorganisms transformed with the subcloned DNA are analyzed for drug-binding ability. Recombinant cultures producing peptide fragments comprising the drug-binding domain thus are identified.

Cultivation of the recombinant cells produces the peptide fragment for use as a polymeric carrier.

While a single drug-binding domain may be attached to a targeting protein, ligand or anti-ligand in certain cases, it is often desirable to attach more then one drug molecule to a targeting protein, ligand or anti-ligand. In such cases, the polymeric carrier preferably comprises more than one drug-binding domain. Conjugates of such polymeric carriers and targeting proteins, ligands or anti-ligands may be used to deliver multiple drug molecules to target cells, thus enhancing the therapeutic effect against the target cells.

These polymeric carriers comprising more than one drug-binding domain may be derived from the peptides containing single domains which are produced by any of the above-described methods. Several drug-binding domains can be covalently joined together, after refolding, using bifunctional linkers to form polymeric carriers. The linkers are selected to give optimal polymerization and generally consist of variable-length spacer groups with a chemically reactive group at each end. The two chemically reactive groups may be the same or different, and each will react with a functional group on a peptide fragment, thereby joining peptide fragments together through the linker.

Among the many possible chemically reactive groups that a linker may comprise are amine-reactive groups such as esters and sulfhydryl-reactive groups such as maleimides. The spacer portion of the linker preferably is large enough to reduce steric hindrance during reaction with the peptide fragments, yet small enough so that the linker molecules used to form a multi-domain polymeric carrier do not significantly increase the molecular weight of the carrier. The spacer may, for example, comprise a chain of from two to four methylene groups or a single cyclohexane ring.

Many suitable linkers are known, examples of which include dimethylsuberimidate, bis-(sulfosuccinimidyl) suberate, and sulfosuccinimidyl -(4'-azido-2'-nitrophenylamino) hexanoate. Other suitable crosslinkers and the use thereof are described in the Pierce Chemical Company 1988 Handbook and General Catalog, pages 222–243. An isolated domain could be polymerized by introducing two surface thiols on opposite faces of the structure (if it doesn't already have cysteines) and air-oxidizing.

The resulting multiple drug-binding domain polymeric carriers should not be so large as to adversely affect the immunoreactivity or other properties of the targeting protein. Advantageously, the polymeric carrier is less than 60 kilodaltons. When water solubility is an important characteristic of the resulting targeting-protein conjugate, the size of the carrier may have to be further reduced.

The total size of the polymeric carrier will vary according to such factors as the therapeutic activity of the particular drug to be used (e.g., whether attachment of multiple drug molecules to the carrier is desirable), the susceptibility of a particular targeting protein, ligand or anti-ligand to loss of targeting ability when a high molecular weight polypeptide (i.e., the carrier) is attached thereto, and the size of the drug-binding peptide(s) from which the polymeric carrier is formed. In one embodiment of the invention, a polymeric carrier comprises from two to twenty, preferably from two to about ten, drug-binding domains. The polymeric carrier preferably has a molecular weight of about 35 kilodaltons or less.

The drug-binding domains employed in the present invention are derived from drug-binding proteins. The term "derived from a protein" as used herein is not limited to actual physical isolation from a protein. The process of producing the polymeric carriers of the invention generally begins with identification of a drug-binding domain within a protein. Once the domain is characterized (e.g., by determination of the amino acid sequence), multiple copies of the domain may be produced by synthetic methods that include peptide synthesis and recombinant DNA technology.

In addition, the polymeric carriers may comprise drug-binding domains that are modifications of the domains found in the parent protein. These modifications include, among others, changes in the amino acid sequence (e.g., to achieve tighter drug binding) or incorporation of additional peptides that confer desirable properties such as improved water solubility on the polymeric carrier. Thus, domains "derived from a protein" may be produced by totally synthetic means, rather than being isolated from the parent protein, and may not be identical to the drug-binding domain found in the parent protein. The polymeric carriers are produced using information obtained through identifying and characterizing drug-binding domains within the parent proteins.

The choice of a particular polypeptide for use as a polymeric carrier may be influenced by several factors. Stability of the non-covalent drug binding to the drug-binding domain is one such factor. When a conjugate of the invention is to be included in a water-soluble pharmaceutical composition, the water solubility of the polymeric carrier component of the conjugate is considered. The polymeric carrier may comprise amino acid sequences extraneous to the actual drug-binding domain. Certain amino acid residues may be added at the termini of the domain-containing peptide, wherein the amino acid residues comprise chemically reactive groups that will react with one of the above-described bifunctional cross-linkers. Alternatively, amino acid sequences may be added to the drug-binding domain in order to achieve the secondary structure required for a particular desirable biological property. Various amino acid sequences may be added during peptide synthesis or DNA synthesis to the peptide fragment originally derived from the drug binding protein. These amino acid sequences may be chosen to increase the water solubility of the resulting polymeric carrier, for example. Such sequences may be chosen based on knowledge of the sequences that confer hydrophilicity on other known proteins, for example.

In some cases, it may be desirable to prepare conjugates of the present invention that comprise more than one type of drug. This is especially advantageous when two or more drugs have a synergistic therapeutic effect on the target cells. Administration of more than one type of drug is desirable in the treatment of certain diseases such as cancer, especially in view of the heterogeneous cell populations found within some tumors.

Thus, a polymeric carrier of the present invention may comprise two or more different types of drug-binding domains. The domains are each isolated from different large molecular weight proteins, then are joined to form a polymeric carrier, using the procedures described above. Alternatively, a particular drug-binding domain may be capable of binding more than one type of drug. Polymeric carriers comprising multiple copies of such a domain may be incubated with the different drugs to bind two or more different types of drugs to the polymeric carrier.

Any suitable procedure may be used for non-covalently binding a drug of interest to the polymeric carrier. In general, an excess of the drug is incubated with the carrier in a buffered aqueous solution to bind the drug to the carrier.

A polymeric carrier of the present invention, having one or more drug molecules bound thereto, is administered to a human or mammalian host for therapeutic purposes. These polymeric carriers are useful as slow-release drug delivery systems.

Alternatively, the polymeric carriers produced by the above-described procedures may be attached to targeting proteins, ligands or anti-ligands or other targeting moieties. The targeting protein serves to deliver the conjugate to a specific cellular or tissue target site when administered in vivo. The targeting is preferably accomplished by immune selectivity through antigen-/antibody interactions.

The "targeting moiety" of the present invention binds to a defined target cell population, such as tumor cells. Preferred targeting moieties useful in this regard include antibody and antibody fragments, proteinaceous ligands or anti-ligands, non-proteinaceous ligands or anti-ligands, peptides, and hormones. Proteins corresponding to or binding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the EGF receptor and which traffic to the nucleus, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

Proteinaceous targeting moieties of the present invention are referred to as "targeting proteins." Suitable targeting proteins include, but are not limited to, antibodies and antibody fragments; serum proteins; enzymes; peptide hormones; and biologic response modifiers. Among the suitable biologic response modifiers which may be used are lymphokines such as interleukins (e.g., IL-1, -2, -3, -4, -5, and -6) or interferons (e.g., alpha, beta, and gamma interferon), erythropoietin, and colony stimulating factors (e.g., G-CSF, GM-CSF, and M-CSF). Peptide hormones include melanocyte stimulating hormone, follicle stimulating hormone, luteinizing hormone, and human growth hormone. Enzymes include fibrinolytic enzymes such as tissue-type plasminogen activator, streptokinase, and urokinase. Serum proteins include human serum albumin.

These proteins may be modified; e.g., to produce variants and fragments of the proteins, as long as the desired biological property (i.e., the ability to bind to the target site) is retained. The proteins may be modified by using various genetic engineering or protein engineering techniques. Another type of modification involves chemically modifying targeting proteins to effect a shift in the isoelectric point of the resulting "charge modified" protein, as described in co-pending U.S. patent application Ser. No. 157,273, filed on Feb. 17, 1988 and now U.S. Pat. No. 5,322,678, entitled "Alteration of Pharmacokinetics of Proteins by Charge Modification". The serum half-life, biodistribution, immunogenicity, and other properties of targeting proteins may be altered by modifying the charge of the protein.

The antibodies employed as targeting proteins in the present invention may be intact antibody molecules, fragments thereof, or functional equivalents thereof, including genetically engineered variations thereof. Examples of antibody fragments are F(ab')$_2$, Fab', Fab, and Fv fragments, which may be produced by conventional procedures or by genetic or protein engineering. While polyclonal antibodies may be employed in the present invention, monoclonal antibodies (MAbs) are preferred. A number of monoclonal antibodies that bind to a specific type of cell have been developed, including MAbs specific for tumor-associated antigens in humans. Among the many such MAbs that may be used are anti-TAC or other interleukin-2 receptor antibodies, 9.2.27 and NR-ML-05 to the 250-kilodalton human melanoma-associated proteoglycan; NR-LU-10 to the 37 to 40-kilodalton pancarcinoma glycoprotein; and OVB3 to an as yet unidentified tumor-associated antigen.

Human monoclonal antibodies or "humanized" murine antibodies are also useful as targeting moieties in accordance with the present invention. For example, murine monoclonal antibody may be "humanized" by genetically recombining the nucleotide sequence encoding the murine Fv region (i.e., containing the antigen binding site which antibodies are also known as chimeric antibodies) or the complementarity determining regions thereof with the nucleotide sequence encoding at least a human constant domain region and an Fc region, e.g., in a manner similar to that disclosed in European Patent Application No. 0,411,893 A2. Some additional murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

The polymeric carriers of the present invention may be attached to ligands or anti-ligands to form drug-polymeric carrier-ligand or -anti-ligand conjugates having diagnostic or therapeutic use. Such polymeric carriers include or are derivatized to include a ligand or anti-ligand conjugation group to facilitate attachment of the compound to a ligand or anti-ligand.

A ligand or anti-ligand conjugation group is a chemically reactive functional group that will react with a ligand or anti-ligand under conditions that do not adversely affect the ligand or anti-ligand, including the capacity of the ligand or anti-ligand to bind to its complementary binding pair member. Ligand or anti-ligand conjugation groups therefore are sufficiently reactive with a functional group on a ligand or anti-ligand so that the reaction can be conducted under relatively mild reaction conditions including those described above for protein-chelate conjugation. For proteinaceous ligands or anti-ligands, such as streptavidin, protein conjugation groups may correspond to ligand or anti-ligand conjugation groups. Examples of suitable ligand or anti-ligand conjugation groups therefore include, but are not limited to, active esters, isothiocyanates, amines, hydrazines, thiols, and maleimides. Among the preferred active esters are thiophenyl ester, 2,3,5,6-tetrafluorophenyl ester, and 2,3,5,6-tetrafluorothiophenyl ester. The preferred active esters may comprise a group that enhances water solubility, at the para (i.e., 4) position on the phenyl ring. Examples of such groups are $CO_2H$, $SO_3^-$, $PO_3^{2-}$, $OPO_3^{2-}$, and $O(CH_2CH_2O)_nCH_3$ groups.

For non-proteinaceous ligand or anti-ligand moieties, such as biotin, suitable conjugations groups are those functional groups that react with a ligand or anti-ligand functional group (e.g., a terminal carboxy group) or a functional group which the ligand or anti-ligand has been derivatized to contain (e.g., an alcohol or an amine group produced by the reduction of a terminal carboxy moiety). As a result, conjugation groups, such as those recited above, that are capable of reacting with —COOH, —OH or —NH$_2$ groups are useful conjugation groups for producing biotin-containing conjugates of this aspect of the present invention. Exemplary biotin-COOH conjugation groups are amines, hydrazines, alcohols and the like. Exemplary biotin-OH conjugation groups are tosylates (Ts), active esters, halides and the like, with exemplary groups being reactive with biotin-O-Ts including amines, hydrazines, thiols and the like. Exemplary biotin-NH$_2$ conjugation groups are active esters, acyl chlorides, tosylates, isothiocyanates and the like.

A variety of procedures may be used to attach the polymeric carrier to a targeting protein, such as an antibody and proteinaceous ligands or anti-ligands such as avidin or streptavidin. Both the polymeric carrier and the targeting protein or proteinaceous ligand or anti-ligand, such as avidin or streptavidin are polypeptides which contain a variety of functional groups, e.g., carboxylic acid (COOH) or free amine (—NH$_2$) groups, which are available for reaction with a suitable functional group to covalently bind the polymeric carrier to the targeting protein. For example, reaction with a water-soluble carbodiimide coupling reagent may be used to form bonds between a free amino group on one reactant species and a COOH group on the other reactant species.

Alternatively, the antibody, the proteinaceous ligand or anti-ligand and/or the polymeric carrier may be derivatized to expose or attach additional reactive functional groups. The derivatization may involve attachment of any of a number of linker molecules, such as those available from Pierce Chemical Company, Rockford, Ill. (see Pierce 1988 General Catalog, pp. 221–250). Alternatively, derivatization may involve chemical treatment of the antibody, ligand or anti-ligand, e.g., oxidative cleavage of vicinal hydroxyls on the sugar moiety of a glycoprotein antibody with periodate to generate free aldehyde groups. The free aldehyde groups on the antibody, ligand or anti-ligand may be reacted with free amine groups on the polymeric carrier to form the desired bond. See U.S. Pat. No. 4,671,958. Procedures for generation of free sulfhydryl groups on antibodies or antibody fragments are also known. See U.S. Pat. No. 4,659,839. Many procedures and linker molecules for attachment of various compounds to proteins such as antibodies or proteinaceous ligands or anti-ligands are known. See, for example, U.S. Pat. Nos. 4,671,958; 4,414,148; 4,046,722; 4,699,784; and 4,680,338.

Biotin has a terminal carboxy moiety which may be reacted with a suitable ligand conjugation group, such as an amine or a hydroxyl in the presence of a coupling agent (e.g., DCC) or the like. In addition, the terminal carboxy moiety may be derivatized to form an active ester, which is suitable for reaction with a suitable ligand conjugation group, such as an amine, a hydroxyl, another nucleophile, or the like. Alternatively, the terminal carboxy moiety may be reduced to a hydroxy moiety for reaction with a suitable ligand conjugation group, such as a halide (e.g., iodide, bromide or chloride), tosylate, mesylate, other good leaving groups or the like. The hydroxy moiety may be chemically modified to form an amine moiety, which may be reacted with a suitable ligand conjugation group, such as an active ester or the like.

A polymeric carrier/drug conjugate or a targeting protein, ligand or anti-ligand/polymeric carrier/drug conjugate of the present invention may be administered for therapeutic purposes to a human or mammalian host by any suitable means. The conjugate may be administered intravenously, intraarterially, or peritoneally, for example, with the choice being determined by such factors as the location of the target site(s) within the body. The dosage will vary according to such factors as the type of drug in the conjugate, the number of drug molecules attached to the polymeric carrier, and the specificity of the targeting protein or the binding affinity of the ligand-anti-ligand pair. Elevated doses, e.g., ranging from about 2 to about 10 times higher, can be used when pretargeting procedures are employed, because of the decoupling of targeting moiety localization and radionuclide localization. A physician skilled in the field to which this invention pertains will be able to determine the proper dosage of a given conjugate.

The conjugates of the present invention may be administered in the form of a suitable pharmaceutical composition. In one embodiment of the invention, a pharmaceutical composition comprises an aqueous solution containing a targeting protein, ligand or anti-ligand/polymeric carrier/drug conjugate or other conjugate of the invention. In an alternative embodiment, the pharmaceutical composition is in solid (e.g., freeze-dried) form, to be dissolved in an aqueous solution prior to injection into the patient. The pharmaceutical preparation may additionally contain conventional stabilizers, excipients, and the like. The preparation is injected into a patient for therapeutic purposes.

One type of therapeutic or diagnostic procedure in which the compounds of the present invention may be employed is a pretargeting protocol. Generally, pretargeting encompasses two protocols, termed the three-step and the two-step. In the three-step protocol, shown in FIG. 1, targeting moiety-ligand is administered and permitted to localize to target. Targeting moiety-ligand conjugates may be prepared in accordance with known techniques therefor. Anti-ligand is then administered to act as a clearing agent and to facilitate and direct the excretion of circulating targeting moiety-ligand. The anti-ligand also binds to target-associated targeting moiety-ligand. Next, a conjugate employing a compound of the present invention is administered, having the following structure:

Ligand—Polymeric Carrier—Drug

Figure 1:
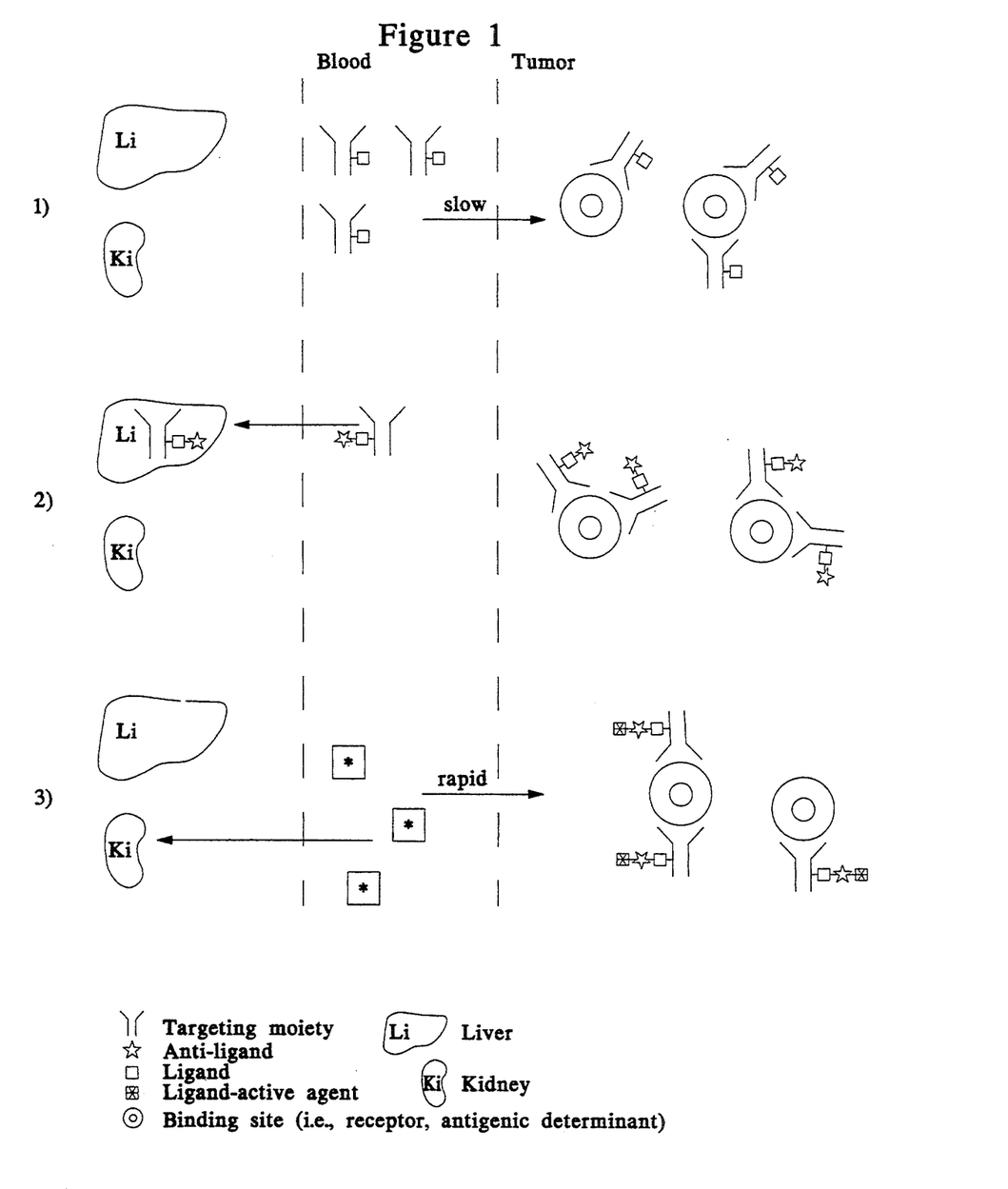
FIG. 1 depicts schematically a three-step protocol wherein targeting moiety-ligand is administered and permitted to localize to target.

The drug-bearing ligand conjugate either binds to target-associated targeting moiety-ligand-anti-ligand or is rapidly excreted, with the excretion proceeding primarily through the renal pathway. Some drug-bearing ligand conjugate may bind to residual circulating anti-ligand-containing conjugate; however, the protocol is designed to minimize such binding. Consequently, the target-non-target ratio of active agent is improved, and undesirable hepatobiliary excretion and intestinal uptake of the active agent are substantially decreased.

Two-step pretargeting involves administration of targeting moiety-anti-ligand, which may be prepared in accordance with known techniques therefor. After permitting the administered agent to localize to target, a ligand-polymer-drug of the present invention is administered. Preferably, as a "step 1.5," a clearing agent is administered to remove circulating targeting moiety-anti-ligand without binding of clearing agent to target-associated targeting moiety-anti-ligand. In this manner, the target-non-target ratio of the active agent bearing ligand is increased, and undesirable hepatobiliary excretion and intestinal uptake of the active agent are substantially decreased.

Data obtained in animal models demonstrate that in vivo anti-ligand binding to a pretargeted targeting moiety-ligand conjugate (i.e., the cell-bound conjugate) may remove the targeting moiety-ligand conjugate from the target cell surface. One possible explanation for the observed phenomenon is that the multivalent anti-ligand crosslinks targeting moiety-ligand conjugates on the cell surface, thereby initiating or facilitating internalization of the resultant complex. The apparent loss of targeting moiety-ligand from the cell surface might result from internal degradation of the conjugate and/or release of active agent from the conjugate (either at the cell surface or intracellularly). An alternative explanation for the observed phenomenon is that permeability changes in the target cell's membrane allow increased passive diffusion of any molecule into the target cell. Also, some loss of targeting moiety-ligand may result from alteration in the affinity by subsequent binding of another moiety to the targeting moiety-ligand, e.g, anti-idiotype monoclonal antibody binding causes removal of tumor bound monoclonal antibody.

The present invention recognizes that this phenomenon (apparent loss of the targeting moiety-ligand from the target cell surface) may be used to advantage with regard to in vivo delivery of therapeutic agents generally, or to drug delivery in particular; provided that the loss is due to proper internalization of the conjugate. For instance, a targeting moiety may be covalently linked to both ligand and a polymeric carrier bearing therapeutic agents and administered to a recipient. Subsequent administration of anti-ligand crosslinks targeting moiety-ligand-polymer/therapeutic agent conjugates bound at the surface, inducing internalization of the conjugate (and thus the active agent). Alternatively, targeting moiety-ligand may be delivered to the target cell surface, followed by administration of anti-ligand-polymeric carrier-therapeutic agent(s).

The following examples illustrate the use of the process of this invention to form novel polymeric carriers to non-covalently bind drugs. Procedures for preparing conjugates comprising a drug non-covalently bound to a polymeric carrier that is attached to a targeting protein such as an antibody or a ligand such as biotin or an anti-ligand such as avidin or streptavidin also are described. These examples are offered by way of illustration of the invention and not by way of limitation.

EXAMPLE 1

Synthesis of an Adriamycin-Binding Polymeric Carrier

In this example, the drug adriamycin (i.e., doxorubicin) is bound to polymeric carriers derived from chicken riboflavin-binding protein (CRBP). Riboflavin-binding protein is used as the source of the polymeric carrier because this compound is known to non-covalently bind adriamycin. Other anthracycline drugs may be used in place of or in addition to adriamycin in the following procedures. The sequence of CRBP is known (Protein Information Resource Data Bank, release 14 (1987)). The sequence of CRBP contains 5 arginines and 7 methionines. Thus, the proteolytic enzyme arg-C-endoprotease and the chemical peptide digestion agent cyanogen bromide are used initially to generate fragments for testing of drug (adriamycin) binding. Other chemical cleavage methods or proteases could also be used. For cleavage of the peptide at Arg residues, the fragments are 56, 20, 7, 5, 37 and 92 amino acid residues long. For methionine cleavage, the amino acid fragments are 21, 122, 7, 4, 17, 5, 17 and 25 residues long.

The CRBP protein cystines are reduced for one day at 37° C. in 6 M guanidine hydrochloride at pH 8.5 in 0.1 M tris buffer with a 100-fold excess of dithiothreitol (DTT) to protein cysteines. The cysteines may be carboxymethylated with a 5-fold excess of iodoacetic acid to DTT thiols for one hour at 37° C. The protein is microdialyzed against water, or an appropriate buffer for digestion. For cyanogen bromide digestion, 200 μg protein is dissolved in 400 μl of 70% formic acid containing 100 moles of cyanogen bromide per mole methionine, and reacted in the dark, under nitrogen for 24 hours at 37° C. After digestion, the mixture is diluted 10-fold with water, lyophilized, run over a Vydac C-4 5 μ0.4×25 cm reversed-phase column. Elution is with a gradient of 1% per minute from water plus 0.1% trifluoroacetic acid (TFA) to 100% acetonitrile plus 0.1% TFA.

Alternatively, 200 μg reduced (or reduced and carboxymethylated) CRBP protein is dissolved in 0.1 M sodium bicarbonate, pH 8.0, and digested with 10 μg submaxillaris protease (an arg-C-endoprotease) for 14 hours. The fragments are purified as above.

The purified protein fragments (obtained by either chemical or enzymatic digestion) are incubated in 0.1 M phosphate or 0.1 M hepes buffer at pH 7.0 for 1 hour with a 100-fold excess of adriamycin and then eluted over an appropriate gel-filtration column. The peptide peak is checked spectro-photometrically for elution peaks at 280 nm and 495 nm to detect bound adriamycin. This procedure can be repeated with other peptide fragments or other digestion product fragments until a tight binding fragment (preferably Kd approximately less than or equal to 1 uM, as measured by equilibrium dialysis or a fluorescence or spectrophotometric titration) is discovered.

Smaller versions (i.e., subfragments) of the peptide fragment may be synthesized by solid-phase synthesis methodology, as mentioned above, to find the minimal size binding domain, which will tightly bind to the drug adriamycin.

Alternatively, peptides about 30–50 amino acid residues in length, overlapping by 15 residues, can be synthesized using the solid-phase peptide synthesis methodology (described above) from the known CRBP sequence. These peptides can be tested for adriamycin binding as above.

The polymerization of the minimal length peptides retaining tight binding to adriamycin is achieved using bifunctional cross-linking reagents. The choice of cross-linking reagent depends on the amino acid composition of the adriamycin-binding domain. If the adriamycin-binding domain contains 2 or more lysine residues, for example, polymerization may be achieved using amine-reactive, bifunctional cross-linking reagents, such as bis(sulfosuccimidyl) subcrate. Polymerization is achieved after binding of the drug binding domain to adriamycin. A 100-fold excess of the drug is incubated with the peptide in a buffered solution, as described above. A 0.1 M solution of peptide/adriamycin, isolated by size-exclusion chromatography, then is mixed with an equimolar solution of bis(sulfosuccimidyl) suberate at pH 8.0–9.0 in 0.05 M hepes buffer. Aliquots are withdrawn periodically for analysis. The aliquots are run on a 20% SDS gel or over a size-exclusion column to monitor the extent of polymerization. A distribution of polymer length results when the conditions are optimized for a particular length polymer. Advantageously, the polymeric carrier comprises less than 20 copies of the drug-binding domain. The resulting polymerized polymeric carrier having adriamycin bound thereto can be purified as necessary by sizeexclusion HPLC.

The polymeric carrier bound to adriamycin is attached to the targeting protein by a similar cross-linking procedure. The procedure may vary according to the type of targeting protein used. One of the methods described above for attaching carriers to targeting proteins as well as proteinaceous or non-proteinaceous ligands or anti-ligands to form conjugates of the invention (e.g., through the use of bifunctional cross-linkers, such as the heterobifunctional cross-linking agent succinimidyl 4-(N-maleimidomethyl)cyclohexane-1-carboxylate (SMCC) available from Pierce Chemical Company) may be used.

EXAMPLE 2

Isolating a DNA Sequence Which Encodes a Polymeric Carrier

A gene encoding human serum albumin is cloned in a plasmid vector using the procedures of Lawn et al. (Nucleic Acids Research, 9:6103–6114, 1981). Human serum albumin (HSA)-specific DNA is isolated by digesting the recombinant vector with the restriction enzyme Pst I. Samples of the HSA-specific cDNA are subjected to further digestion with several different restriction enzymes in separate reaction mixtures. The resulting DNA fragments are separated by electrophoresis on agarose gels, purified from the gel, and subcloned into plasmid expression vectors comprising regulatory signals functional in E. coli cells, such as the trp promoter-operator. E. coli HB101 cells are transformed with the resulting plasmids and cultured to produce the HSA protein fragments encoded by the HSA gene fragments. These protein fragments are purified from samples of each culture by a standard procedure, such as immunoprecipitation, followed by SDS polyacrylamide gel electrophoresis. See Kessler, J. Immunology 117:1432-90, 1976; and Laemmli, Nature 277:680-85, 1970.

Each protein fragment is analyzed to determine its ability to bind a drug of interest by one of the procedures described above. For example, the drug adriamycin is combined with each protein fragment and the samples are each analyzed to detect free versus protein-bound drug. One method of analysis involves subjecting the protein fragment samples (either purified or in the form of the *E. coli* cell lysates) to electrophoresis on an SDS-polyacrylamide gel. The fragments (separated according to molecular weight) are transferred from the gel to a nitrocellulose sheet in accordance with the known "Western blot" technique. A solution containing adriamycin is contacted with the nitrocellulose sheet. After washing the nitrocellulose sheet to remove non-bound drug, the polypeptide bands which bind the drug will appear red, the color imparted by adriamycin. The culture(s) found to produce a relatively small protein fragment with sufficient affinity for the drug are cultured to produce the polymeric carrier (i.e., the HSA protein fragment) on a larger scale. Alternatively, the amino acid sequence of the peptide fragment may be determined, and the fragment may be produced by peptide synthesis procedures.

When a polymeric carrier comprising multiple drug-binding domains is desired, multiple copies of the peptide fragment produced above may be joined together using a bifunctional cross-linker. A number of different cross-linkers may be used, depending on the amino acid sequence of the peptides to be joined. The linker may be chosen from those described in the Pierce Chemical Company Catalog, as discussed above. One cross-linking procedure is presented in Example 1.

An alternative method for producing the polymeric carrier involves determining the amino acid sequence of the peptide fragment, synthesizing a DNA sequence that encodes a polypeptide comprising at least one copy of the peptide fragment, expressing the DNA sequence in recombinant host cells (thereby producing the polypeptide), and purifying the polypeptide from the recombinant cells for use as a polymeric carrier. The DNA sequence may encode a polymeric carrier comprising multiple drug-binding domains. Alternatively, multiple copies of a single drug-binding peptide fragment produced by the recombinant cells may be purified and enzymatically ligated together to form multi-domain polymeric carriers.

EXAMPLE 3

Preparation of a Polymeric-Carrier-Antibody Conjugate

A polymeric carrier such as one produced as described in Example 1 or 2 is covalently bound to an antibody as follows. This is an alternative procedure to the methods for forming conjugates described in Example 1.

The polymeric carrier is conjugated to a monoclonal antibody through a thioether linkage. The polymeric carrier is first reacted with succinimidyl 4-(N-maleimido-methyl)cyclohexane-1-carboxylate (SMCC) at a molar ratio of 1:10 (carrier:linker). Excess heterobifunctional linker reagent is removed from derivatized polymeric carrier by gel filtration. The antibody is treated with 25 mM dithio-threitol (DTT) in 0.01 M phosphate-buffered saline (PBS), pH 7.5, and excess DTT is removed by gel filtration. The derivatized polymeric carrier and the reduced antibody components are mixed and incubated at room temperature for 15+ minutes.

The conjugation reaction mixtures are then fractionated by FPLC gel filtration on a TSK 3000 column at 0.5 ml/min to separate the immunoconjugate from unconjugated antibody and unreacted derivatized carrier.

If a drug were not bound to the polymeric carrier prior to the step of conjugation to the antibody, the resulting immunoconjugate is mixed with the drug in a buffered solution, whereby the drug becomes associated with the polymeric carrier. Non-bound drug is removed by gel filtration or dialysis. The thus-produced conjugate of the present invention may be administered to a patient bearing a target site to which the antibody binds, wherein the target site is to be treated with the drug. The antibody may be a monoclonal antibody that binds to a tumor, and the drug is an anti-cancer drug.

EXAMPLE 4

Polymeric Carriers Isolated from HSA

The full-length protein human serum albumin (HSA) is purified from human blood plasma or from recombinant cells by known procedures. See, for example, U.S. Pat. No. 4,684,723; and Lawn et al., Nucleic Acids Research, vol. 9, No 22, 1981. The protein is subjected to digestion with a proteolytic enzyme to generate polypeptide fragments which are separated by electrophoresis (e.g., on an SDS-polyacrylamide gel). The ability of each polypeptide fragment to bind a particular drug of interest is analyzed by procedures which detect protein-bound drug versus free drug, such as those described in Examples 1 and 2. The drug is a drug that the parent protein binds non-covalently (see Table I).

Drug-binding polypeptide fragments suitable for use as polymeric carriers thus are identified. If desired, smaller peptide fragments may be generated by enzymatic or chemical cleavage of the thus-identified drug-binding polypeptide fragment. The drug-binding assay is repeated on the smaller fragments to identify the smallest peptide fragment comprising a drug-binding domain. The amino acid sequence of each carrier is determined using the standard Edman degradation process, as described above. Once the amino acid sequence is determined, the carriers are synthesized as needed using a commercially available peptide synthesizer. Multi-domain polymeric carriers may be produced by joining multiple copies of the peptide together using bifunctional linkers.

Alternatively, a DNA sequence which encodes the desired amino acid sequence (preferably multiple copies thereof) is synthesized in vitro. The synthesized DNA sequence is inserted into an appropriate expression vector and appropriate host cells are transformed with the recombinant vector. The cells are subjected to an appropriate screening process to identify recombinant cells producing the carrier polypeptide of interest. For example, lysates of samples of the cultures may be subjected to gel electrophoresis to identify those producing a polypeptide of the size expected for the carrier polypeptide. Further analysis may involve one of the above-described drug-binding assays.

A recombinant microbial strain producing the desired carrier polypeptide is cultured on a larger scale to produce the carrier polypeptide as needed.

EXAMPLE 5

Pharmaceutical Composition Comprising Polymeric Carrier and Drug

A single- or multi-domain version of the polymeric carrier derived from RBP is reacted with doxorubicin and/or other anthracyclines as described in Example 1. Unbound drug is removed by gel filtration. Carrier-bound drug is then lyophilized with a typical additive such as lactose. Upon reconstitution to form an aqueous solution, the composition is administered to patients with tumors. Improved tumor delivery and less cardiac toxicity (compared to administration of the free drug) are expected to be achieved, thereby allowing higher dose levels as well as administration to patients who are no longer eligible for treatment with adriamycin because of cumulative cardiac toxicity. The slow release of the drug from the polymeric carrier also maintains higher serum concentrations for longer periods of time.

the methods for forming conjugates described in Example 1.

A. Preparation of SMCC-derivatized streptavidin.

31 mg (0.48 μmol) streptavidin was dissolved in 9.0 ml PBS to prepare a final solution at 3.5 mg/ml. The pH of the solution was adjusted to 8.5 by addition of 0.9 ml of 0.5 M borate buffer, pH 8.5. A DMSO solution of SMCC (3.5 mg/ml) was prepared, and 477 μl (4.8 μmol) of this solution was added dropwise to the vortexing protein solution. After 30 minutes of stirring, the solution was purified by G-25 (PD-10, Pharmacia, Piscataway, New Jersey) column chromatography to remove unreacted or hydrolyzed SMCC. The purified SMCC-derivitized streptavidin was isolated (28 mg, 1.67 mg/ml).

B. Preparation of Streptavidin-Polymeric Carrier-Drug Conjugate.

The SMCC-derivatized streptavidin is employed to form the desired product in the following reaction scheme:

EXAMPLE 6

Preparation of a Polymeric Carrier-Streptavidin Conjugate

A polymeric carrier such as one produced as described in Example 1 or 2 is covalently bound to streptavidin as follows. This is an alternative procedure to where the dotted line indicates non-covalent association between the drug and the drug binding domain and where y ranges from 1 to about 2, x ranges from about 5 to about 125, wherein R is the side chain of an amino acid n ranges from 1 to about 20, and n' ranges from about 1 to about 20 with n' being less than or equal to n. The amino acid residues delimited by x constitute individual drug binding domains that non-covalently associate with the drug molecules as well as additional amino acid residues, if any, included for synthetic convenience or other purposes. There are n' drug binding domains which bind n drugs. The binding of streptavidin to the proteinaceous polymeric carrier takes place via a free lysine residue on the polymeric carrier.

The preparation of a polymeric carrier and the binding thereto to adriamycin, for example, has been described in Example 1, with the solubility of adriamycin potentially limiting the number of drug molecules that may be bound to this embodiment of the polymeric carrier of the present invention. The remaining lysine residues on the drug bound polymeric carrier are derivatized with iminothiolane (Traut's reagent available from Pierce Chemical Company) to produce free thiols on the drug bound polymeric carrier. If cysteine residues are available for binding, derivatization of the lysine residues is unnecessary. The thiols are then conjugated to the SMCC-derivatized streptavidin under suitable conditions to form a thioether linkage between the polymer and streptavidin.

If a drug is not bound to the polymeric carrier prior to the step of conjugation to streptavidin, the resulting immunoconjugate is mixed with the drug in a buffered solution, whereby the drug becomes associated with the polymeric carrier. Non-bound drug is removed by gel filtration or dialysis. The thus-produced conjugate of the present invention may be administered to a patient bearing a pretargeted biotin site to which streptavidin binds.

EXAMPLE 7

Ligand-Polymeric Carrier Conjugation

Drugs are associated with the polymeric carrier by a non-covalent interaction of the drug to the binding domain of the polymeric carrier having an affinity for that drug, as described in earlier examples. Provided that lysine residues are present on the polymeric carrier and are available for binding to ligand such as biotin, the biotin-polymeric carrier-drug conjugate is formed in one step as shown below.

where the dotted line indicates non-covalent association between the drug and the drug binding domain and where y ranges from 0 to about 10, x ranges from about 5 to about 125, wherein R is the side chain of an amino acid n ranges from 1 to about 10, and n' ranges from 1 to about 10 (based upon the limited solubility of adriamycin), with n' being less than or equal to n. The amino acid residues delimited by x constitute individual drug binding domains that non-covalently associate with the drug molecules as well as additional amino acid residues, if any, included for synthetic convenience or other purposes. There are n' drug binding domains which bind n drugs.

The drug bound polymeric carrier is reacted with biotin-NHS ester (available from Sigma Chemical Company) at basic pH to form the product conjugate.

Alternatively, if a drug is not bound to the polymeric carrier prior to the step of conjugation to biotin, the resulting immunoconjugate is mixed with the drug in a buffered solution, whereby the drug becomes associated with the polymeric carrier. Non-bound drug is removed by gel filtration or dialysis. The thus-produced conjugate of the present invention may be administered to a patient bearing a pretargeted avidin or streptavidin site to which biotin binds.

EXAMPLE 8

Polymeric Carrier Targeting Moiety-Ligand Conjugate for Two-Step Pretargeting In Vivo A. Preparation and Characterization of Biotinylated Antibody.

Biotinylated NR-LU-10 was prepared according to either of the following procedures. The first procedure involved derivatization of antibody via lysine ε-amino groups. NR-LU-10 was radioiodinated at tyrosines using chloramine T and either $^{125}$I or $^{131}$I sodium iodide. The radioiodinated antibody (5–10 mg/ml) was then biotinylated using biotinamido caproate NHS ester in carbonate buffer, pH 8.5, containing 5% DMSO, according to the scheme below.

The impact of lysine biotinylation on antibody immunoreactivity was examined. As the molar offering of biotin:antibody increased from 5:1 to 40:1, biotin incorporation increased as expected (measured using the HABA assay and pronase-digested product) (Table 1, below). Percent of biotinylated antibody immunoreactivity as compared to native antibody was assessed in a limiting antigen ELISA assay. The immunoreactivity percentage dropped below 70% at a measured derivatization of 11.1:1; however, at this level of derivatization, no decrease was observed in antigen-positive cell binding (performed with LS-180 tumor cells at antigen excess). Subsequent experiments used antibody derivitized at a biotin:antibody ratio of 10:1.

TABLE 1

| Effect of Lysine Biotinylation on Immunoreactivity | | | |
|---|---|---|---|
| Molar Offering (Biotins/Ab) | Measured Derivatization (Biotins/Ab) | Immunoassessment (%) | |
| | | ELISA | Cell Binding |
| 5:1 | 3.4 | 86 | |
| 10:1 | 8.5 | 73 | 100 |
| 13:1 | 11.1 | 69 | 102 |
| 20:1 | 13.4 | 36 | 106 |
| 40:1 | 23.1 | 27 | |

Alternatively, NR-LU-10 was biotinylated using thiol groups generated by reduction of cystines. Derivatization of thiol groups was hypothesized to be less compromising to antibody immunoreactivity. NR-LU-10 was radioiodinated using p-aryltin phenylate NHS ester (PIP-NHS) and either $^{125}$I or $^{131}$I sodium iodide. Radioiodinated NR-LU-10 was incubated with 25 mM dithiothreitol and purified using size exclusion chromatography. The reduced antibody (containing free thiol groups) was then reacted with a 10- to 100-fold molar excess of N-iodoacetyl-n'-biotinyl hexylene diamine in phosphate-buffered saline (PBS), pH 7.5, containing 5% DMSO (v/v).

TABLE 2

| Effect of Thiol Biotinylation on Immunoreactivity | | | |
|---|---|---|---|
| Molar Offering (Biotins/Ab) | Measured Derivatization (Biotins/Ab) | Immunoassessment (%) | |
| | | ELISA | Cell Binding |
| 10:1 | 4.7 | 114 | |
| 50:1 | 6.5 | 102 | 100 |
| 100:1 | 6.1 | 95 | 100 |

As shown in Table 2, at a 50:1 or greater biotin:antibody molar offering, only 6 biotins per antibody were incorporated. No significant impact on immunoreactivity was observed.

The lysine- and thiol-derivitized biotinylated antibodies ("antibody (lysine)" and "antibody (thiol)", respectively) were compared. Molecular sizing on size exclusion FPLC demonstrated that both biotinylation protocols yielded monomolecular (monomeric) IgGs. Biotinylated antibody (lysine) had an apparent molecular weight of 160 kD, while biotinylated antibody (thiol) had an apparent molecular weight of 180 kD. Reduction of endogenous sulfhydryls to thiol groups, followed by conjugation with biotin, may produce a somewhat unfolded macromolecule. If so, the antibody (thiol) may display a larger hydrodynamic radius and exhibit an apparent increase in molecular weight by chromatographic analysis. Both biotinylated antibody species exhibited 98% specific binding to immobilized avidin-agarose.

Further comparison of the biotinylated antibody species was performed using non-reducing SDS-PAGE, using a 4% stacking gel and a 5% resolving gel. Biotinylated samples were either radiolabeled or unlabeled and were combined with either radiolabeled or unlabeled avidin or streptavidin. Samples were not boiled prior to SDS-PAGE analysis. The native antibody and biotinylated antibody (lysine) showed similar migrations; the biotinylated antibody (thiol) produced two species in the 50–75 kD range. These species may represent two thiol-capped species. Under these SDS-PAGE conditions, radiolabeled streptavidin migrates as a 60 kD tetramer. When 400 μg/ml radiolabeled streptavidin was combined with 50 μg/ml biotinylated antibody (analogous to "sandwiching" conditions iN vivo), both antibody species formed large molecular weight complexes. However, only the biotinylated antibody (thiol)-streptavidin complex moved from the stacking gel into the resolving gel, indicating a decreased molecular weight as compared to the biotinylated antibody (lysine)-streptavidin complex.

B. Blood Clearance of Biotinylated Antibody Species.

Radioiodinated biotinylated NR-LU-10 (lysine or thiol) was intravenously administered to non-tumored nude mice at a dose of 100 μg. At 24 h post-administration of radioiodinated biotinylated NR-LU-10, mice were intravenously injected with either saline or 400 μg of avidin. With saline administration, blood clearances for both biotinylated antibody species were biphasic and similar to the clearance of native NR-LU-10 antibody.

In the animals that received avidin intravenously at 24 h, the biotinylated antibody (lysine) was cleared (to a level of 5% of injected dose) within 15 min of avidin administration (avidin:biotin=10:1). With the biotinylated antibody (thiol), avidin administration (10:1 or 25:1) reduced the circulating antibody level to about 35% of injected dose after two hours. Residual radiolabeled antibody activity in the circulation after avidin administration was examined in vitro using immobilized biotin. This analysis revealed that 85% of the biotinylated antibody was complexed with avidin. These data suggest that the biotinylated antibody (thiol)-avidin complexes that were formed were insufficiently crosslinked to be cleared by the RES.

Blood clearance and biodistribution studies of biotinylated antibody (lysine) 2 h post-avidin or post-saline administration were performed. Avidin administration significantly reduced the level of biotinylated antibody in the blood, and increased the level of biotinylated antibody in the liver and spleen. Kidney levels of biotinylated antibody were similar.

C. Preparation of Biotinylated Antibody (Thiol) Through Endogenous Antibody Sulfhydryl Groups Or Sulfhydryl-Generating Compounds.

Certain antibodies have available for reaction endogenous sulfhydryl groups. If the antibody to be biotinylated contains endogenous sulfhydryl groups, such antibody is reacted with N-iodoacetyl-n'-biotinyl hexylene diamine.

The availability of one or more endogenous sulfhydryl groups obviates the need to expose the antibody to a reducing agent, such as DTT, which can have other detrimental effects on the biotinylated antibody.

Alternatively, one or more sulfhydryl groups are attached to a targeting moiety through the use of chemical compounds or linkers that contain a terminal sulfhydryl group. An exemplary compound for this purpose is iminothiolane. As with endogenous sulfhydryl groups (discussed above), the detrimental effects of reducing agents on antibody are thereby avoided.

D. Conjugation of the Monoclonal Antibody-Biotin Conjugate to a Polymeric Carrier.

The monoclonal antibody-biotin conjugate is dissolved in PBS. The pH of the solution is adjusted to 8.5 by addition of 0.5 M borate buffer, pH 8.5. A DMSO solution of SMCC is prepared, and this solution is added dropwise to the vortexing protein solution. After 30 minutes of stirring, the solution is purified by G-25 (PD-10, Pharmacia, Piscataway, New Jersey) column chromatography to remove unreacted or hydrolyzed SMCC. The purified SMCC-derivitized monoclonal antibody-biotin conjugate is isolated. Lysine residues on the polymeric carrier are derivatized with iminothiolane (Traut's reagent available from Pierce Chemical Company) to produce free thiols on the polymeric carrier. If cysteine residues are available for binding, derivatization of the lysine residues is unnecessary. The thiols are then conjugated to the SMCC-derivatized monoclonal antibody-biotin conjugate under suitable conditions to form a thioether linkage between the polymer and the monoclonal antibody.

E. Drug Binding.

The resulting immunoconjugate is mixed with the drug in a buffered solution, whereby the drug becomes associated with the polymeric carrier. Nonbound drug is removed by gel filtration or dialysis. The thus-produced conjugate of the present invention may be administered to a patient bearing a target site to which the antibody binds.

EXAMPLE 9

Three-Step Pretargeting

A patient presents with ovarian cancer. A monoclonal antibody (MAb) directed to an ovarian cancer cell antigen is conjugated to biotin to form a MAb-biotin conjugate. The MAb-biotin conjugate is administered to the patient in an amount in excess of the maximum tolerated dose of conjugate administrable in a targeted, direct label protocol (e.g., administration of monoclonal antibody-chelate-radionuclide conjugate) and is permitted to localize to target cancer cells for 24–48 hours. Next, an amount of avidin sufficient to clear nontargeted MAb-biotin conjugate and to bind to the targeted biotin is administered. A biotin-polymeric carrier-drug conjugate of the type discussed in Example 7 above is dispersed in a pharmaceutically acceptable diluent and administered to the patient in a therapeutically effective dose. The biotin-polymeric carrier-drug conjugate localizes to the targeted MAb-biotin-avidin moiety or is removed from the patient via the renal pathway.

EXAMPLE 10

Two-Step Pretargeting

A patient presents with colon cancer. A monoclonal antibody (MAb) directed to a colon cancer cell antigen is conjugated to biotin to form a MAb-biotin conjugate. The MAb-biotin conjugate is administered to the patient in an amount in excess of the maximum tolerated dose of conjugate administrable in a targeted, direct label protocol (e.g., administration of monoclonal antibody-chelate-radionuclide conjugate) and is permitted to localize to target cancer cells for 24–48 hours. A streptavidin-polymeric carrier-drug conjugate of the type discussed in Example 6 above is dispersed in a pharmaceutically acceptable diluent and administered to the patient in a therapeutically effective dose. The streptavidin-polymeric carrier-drug conjugate localizes to the targeted MAb-biotin moiety or is removed from the patient via the patient's excretory system.

EXAMPLE 11

Two-Step Pretargeting

A patient presents with colon cancer. A monoclonal antibody (MAb) directed to a colon cancer cell antigen is conjugated to biotin and to a polymeric carrier. Drug is then non-covalently associated with the polymeric carrier portion of the conjugate to form a drug-polymeric carrier-MAb-biotin conjugate as described in Example 8 above. The drug-polymeric carrier-MAb-biotin conjugate is administered to the patient in an amount approaching the maximum tolerated dose of conjugate administrable in a targeted, direct label protocol (e.g., administration of monoclonal antibody-chelate-radionuclide conjugate) and is permitted to localize to target cancer cells for 24–48 hours. Streptavidin is dispersed in a pharmaceutically acceptable diluent and administered to the patient in a dose effective to cross-link the biotins that are now associated with the target site. The streptavidin localizes to the targeted drug-polymeric carrier-MAb-biotin moiety conjugates and cross-links those conjugates, thereby inducing internalization thereof.

From the foregoing, it will be appreciated that, although specific embodiments of the invention have been described herein for purposes of illustration, various modifications may be made to the invention without departing from the spirit and scope of the invention.

What is claimed is:

1. ° C. A ligand or an anti-ligand/polymeric carrier/drug conjugate comprising a ligand consisting of biotin or an anti-ligand selected from the group consisting of avidin and streptavidin, which ligand or anti-ligand is covalently bound to a polymeric carrier that comprises at least one drug-binding domain derived from a drug-binding protein, and at least one drug non-covalently bound to the polymeric carrier, wherein the polymeric carrier does not comprise an entire drug-binding protein, but is derived from a drug-binding domain of said drug-binding protein which derivative non-covalently binds a drug which is non-covalently bound by an entire naturally occurring drug-binding protein, and wherein the molecular weight of the polymeric carrier is less than about 60,000 daltons, and wherein said drug is selected from the group consisting of an anti-cancer anthracycline antibiotic, cis-platinum, methotrexate, vinblastine, mitoxanthrone ARA-C, 6-mercaptopurine, 6-mercaptoguanosine, mytomycin C and a steroid.

2. A ligand or an anti-ligand/polymeric carrier/drug conjugate comprising a ligand or anti-ligand which ligand is biotin and said anti-ligand is selected from the group consisting of avidin and streptavidin, which ligand or anti-ligand is covalently bound to a polymeric carrier and at least one non-antibody drug non-covalenfly bound to the polymeric carder, wherein the polymeric carrier comprises from 2 to about 20 drug-binding domains derived from one or more naturally occurring drug-binding protein(s);

wherein the polymeric carder does not comprise an entire drug-binding protein, but comprises 2 to about 20 drug-binding domains derived from said one or more naturally occurring drug-binding protein(s), which domains non-covalently bind to one or more non-antibody drugs which are non-covalently bound by said one or more naturally occurring drug-binding protein(s), and wherein the molecular weight of the polymeric carder is less than about 60,000 daltons.

3. The conjugate of claim 1 or 2 wherein the drug is selected from the group consisting of doxorubicin, daunorubicin, other anthracyclines, cis-platinum, and methotrexate, and the drug-binding protein is an albumin.

4. The conjugate of claim 1 or 2 wherein the drug is a steroid and the drug-binding protein is a steroid-binding protein.

5. The conjugate of claim 4 wherein the drug is an estrogen and the drug-binding protein is an estrogen receptor.

6. The conjugate of claim 1 or 2 wherein the drug is selected from the group consisting of doxorubicin, daunorubicin, other anthracycl ines, vinblastine, mitoxantrone, ARA-C, 6-mercaptopurine, mercaptoguanosine, and mitomycin C, and the drug-binding protein is $\alpha$-1-acid glycoprotein.

7. The conjugate of claim 1 or 2 wherein the drug is selected from the group consisting of doxorubicin, daunorubicin, and other anthracylines, and the drug-binding protein is riboflavin-binding protein.

8. The conjugate of claim 2 wherein the polymeric carrier comprises from 2 to about 10 drug-binding domains.

9. The conjugate of claim 2 wherein the drug-binding domains are joined through bifunctional crosslinkers.

10. The conjugate of claim 2 wherein the polymeric carrier has two or more different anti-cancer drugs bound thereto.

11. The conjugate of claim 1 or 2 wherein the polymeric carrier further comprises a peptide that increases the water solubility of the polymeric carrier.

12. A slow-release pharmaceutical composition having therapeutic use comprising a conjugate of claim 1 or 2 in a pharmaceutically acceptable solution.

13. The ligand or anti-ligand/polymeric carder/drug conjugate of claim 2 wherein the polymeric carder contains more than 2 drug-binding domains.

14. The ligand or anti-ligand/polymeric carrier/drug conjugate of claim 2 wherein the polymeric carrier is non-covalently bound to more than two non-antibody drug molecules.

* * * * *